United States Patent [19] [11] 4,126,221
Cerwin [45] Nov. 21, 1978

[54] PACKAGE FOR MULTIPLE SURGICAL SUTURES

[75] Inventor: Robert J. Cerwin, Pittstown, N.J.

[73] Assignee: Ethicon, Inc., Somerville, N.J.

[21] Appl. No.: 849,562

[22] Filed: Nov. 8, 1977

Related U.S. Application Data

[63] Continuation-in-part of Ser. No. 787,171, Apr. 13, 1977, abandoned.

[51] Int. Cl.² .............................................. A61L 17/02
[52] U.S. Cl. ................................... 206/63.3; 206/388; 128/335.5; 242/174
[58] Field of Search ...................... 206/63.3, 491, 353, 206/392, 388; 128/335.5; 242/174, 159

[56] References Cited

U.S. PATENT DOCUMENTS

| 2,590,799 | 3/1952 | Solowey | 206/63.3 |
| 2,617,523 | 11/1952 | Zoller | 206/63.3 |
| 2,702,627 | 2/1955 | Kennison et al. | 206/63.3 |
| 3,162,307 | 12/1964 | Regan, Jr. | 206/63.3 |
| 3,206,018 | 9/1965 | Lewis et al. | 206/63.3 |
| 3,280,971 | 10/1966 | Regan, Jr. | 206/63.3 |
| 3,444,994 | 5/1969 | Kaepernik et al. | 206/63.3 |
| 3,627,120 | 12/1971 | Bordeau | 206/63.3 |
| 4,034,850 | 7/1977 | Mandel et al. | 206/63.3 |

Primary Examiner—William Price
Assistant Examiner—Joseph Man-Fu Moy
Attorney, Agent, or Firm—Wayne R. Eberhardt

[57] ABSTRACT

A package for multiple strands of surgical sutures which provides for delivery of individual suture strands. The several sutures are contained within a single compartment of the package, with each suture being individually wound in the form of a coil comprising a series of convolutions, each convolution being laterally displaced from adjacent convolutions and disposed in sequence over the length of the suture. Each individual suture within the package compartment is laterally displaced from adjacent sutures in a contiguous, partially overlapping relationship. The desired suture coil configuration and positioning within the package compartment is conveniently obtained by sequentially winding individual sutures around two vertical winding pins in an upwardly spiraling pattern, with successive loops of each suture and successive sutures being displaced laterally along the pins. The wound sutures are packaged in a suture folder which is adapted to maintain the individual sutures in their wound configuration and in their relative positions with one end of each suture extending from the folder whereby individual suture strands may be grasped and withdrawn from the package without entangling sutures remaining in the package.

19 Claims, 7 Drawing Figures

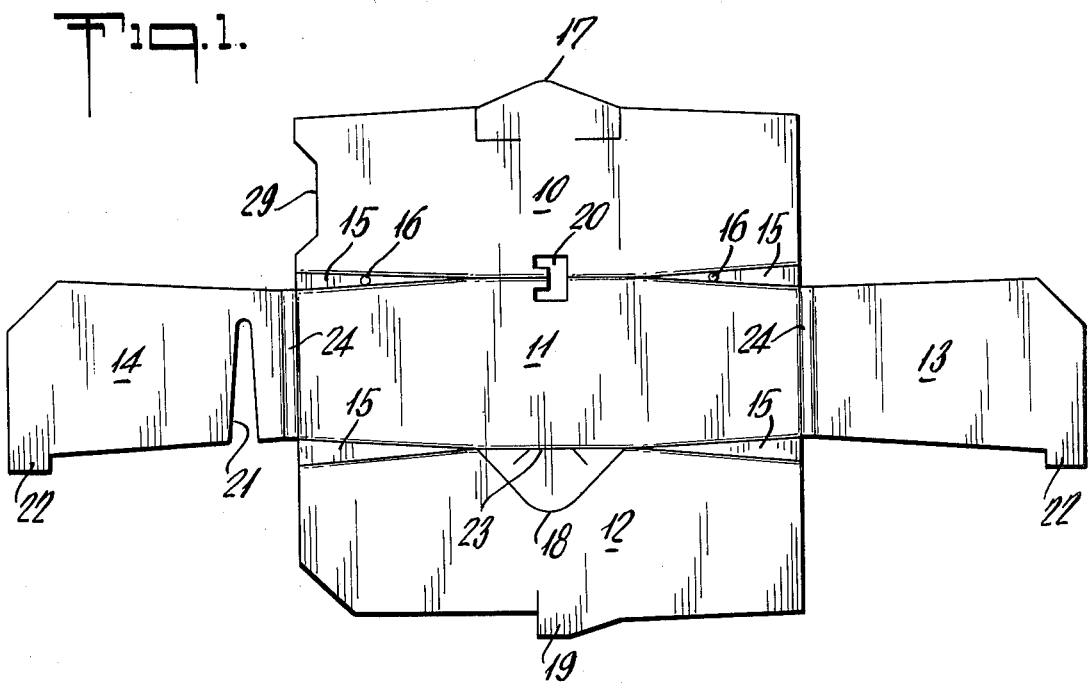
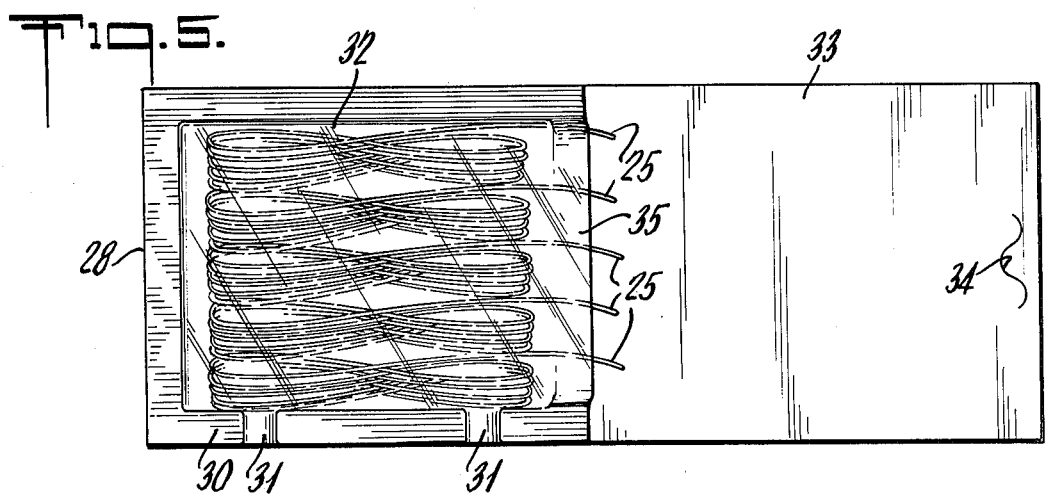
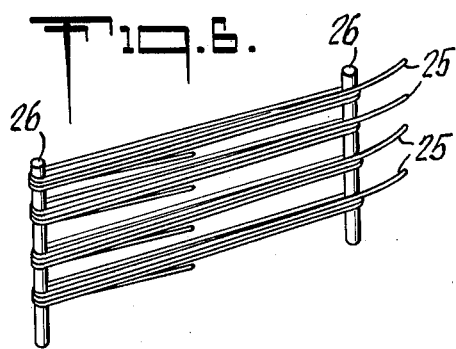
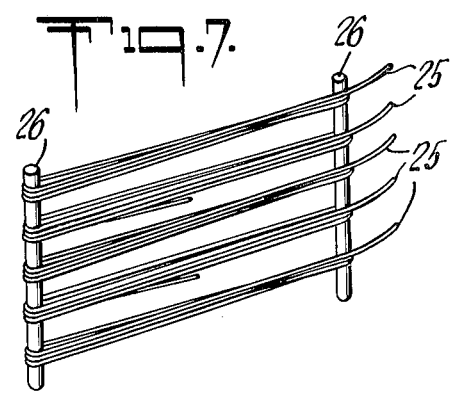

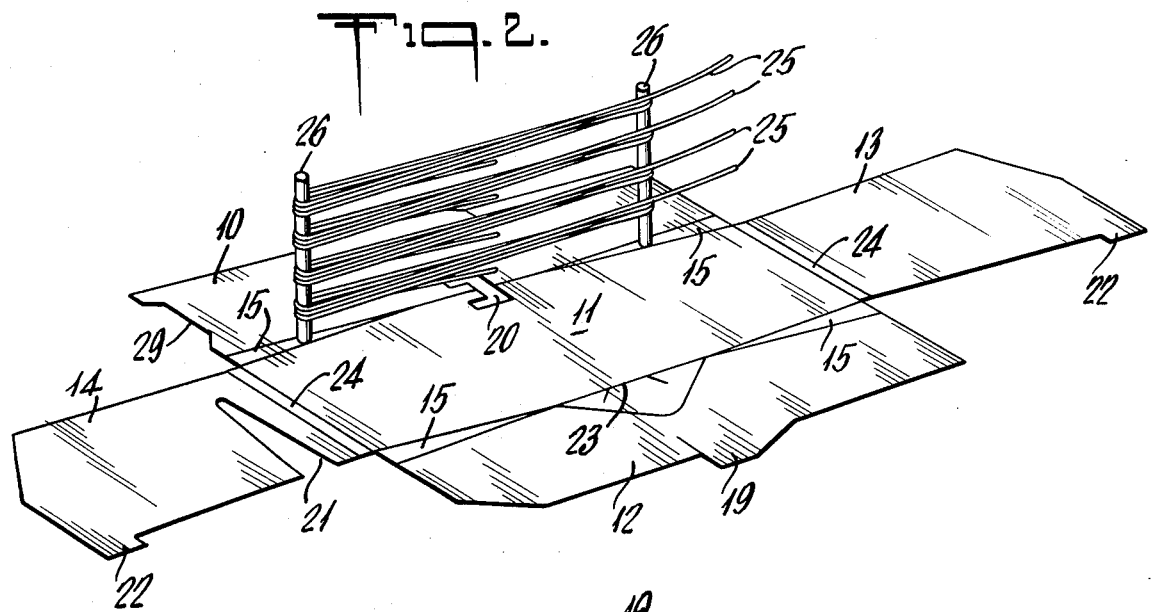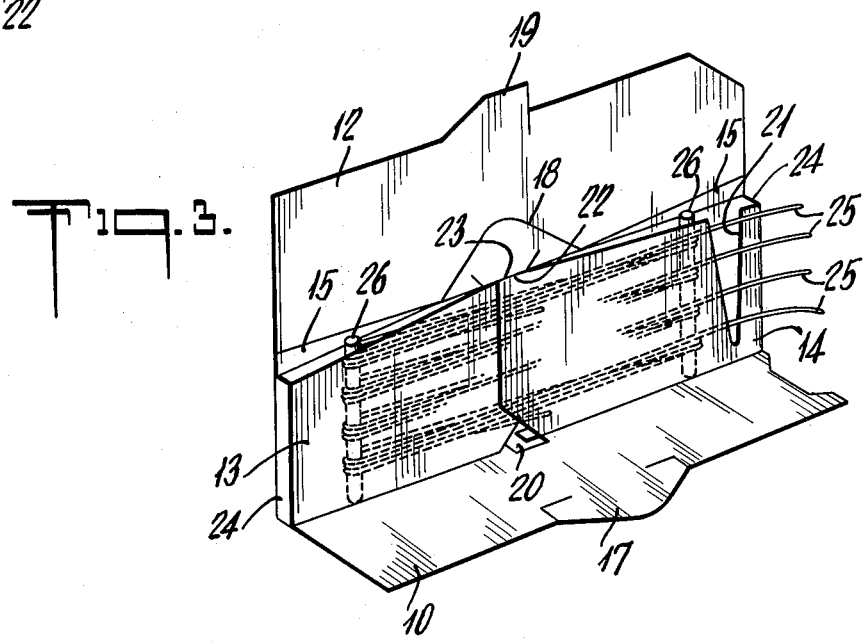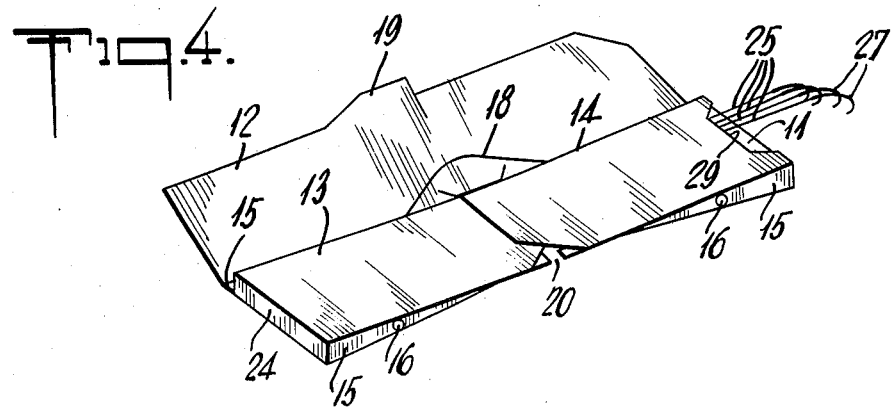

PACKAGE FOR MULTIPLE SURGICAL SUTURES

CROSS-REFERENCE TO RELATED APPLICATIONS

This application is a continuation-in-part of Ser. No. 787,171, filed Apr. 13, 1977, now abandoned.

BACKGROUND OF THE INVENTION

1. Field of the Invention

The present invention relates to packages for surgical sutures, and more particularly to packages for multiple strands of sutures which allow single strand dispensing.

2. Description of Prior Art

In many surgical procedures, the surgeon employs a large number of sutures in making the wound closure. Suture manufacturers recognized this practice and offer many sutures in multistrand packages. This is a matter of convenience to the surgeons and operating room personnel in that they are required to open fewer packages and the multistrand packages serve to keep individual sutures from becoming scattered during the course of the operation.

One problem associated with multiple suture packaging has been to provide a means for allowing individual sutures to be removed from the packages without entanglement. In other words, the multistrand suture package must provide for single strand dispensing. This characteristic of the package has been obtained heretofore by providing individual compartments within the package for each suture as illustrated, for example, in U.S. Pat. Nos. 3,857,484 and 3,759,376. An alternative method is to provide a single channel or tube for the length of the sutures as described, for example, in U.S. Pat. Nos. 3,280,971, 3,338,401 and 3,972,418.

The present invention is concerned with multistrand suture packages of a novel type wherein the suture strands are neither placed in individual compartments nor contained in a single channel or tube, but which nevertheless, allow for single strand dispensing. Moreover, the packages of the present invention are easily loaded by hand or machine and may be used with either needled or unneedled sutures. It is accordingly an object of the present invention to provide a new and improved package for multiple strands of surgical sutures which provides for single strand delivery.

SUMMARY

In accordance with the present invention, packages are provided wherein a plurality of suture strands are maintained within a single compartment of the package as individual and adjacent filaments with each filament wound in the form of an elongated coil having a longitudinal axis and comprising a plurality of overlapping convolutions disposed in sequence from one end of the suture to the other with the longitudinal axis of adjacent convolutions being laterally displaced one from the other, and with individual sutures being laterally displaced from adjacent sutures in a contiguous and partially overlapping relationship.

The desired suture configuration is conveniently obtained by sequentially winding individual sutures around two vertical pins beginning at the bottom of the pins and winding in an upward spiral to provide a plurality of convolutions disposed in sequence over the length of the suture and along the axis of the pins with substantially no overlap between adjacent convolutions of individual sutures or between adjacent sutures. The sutures may be wound around the pins as a series of figure-8 convolutions, as a series of circular loops, as a series of circular loops having at least one reversal in the direction of winding, or as a combination of these.

A suture package is positioned to enclose the sutures and winding pins between two panels of the package in order to retain the sutures in position when the pins are removed. Once the winding pins are removed, adjacent sutures assume a contiguous and partially overlapping relationship within the compartment of the package formed by the two panels. One end of each suture extends from one end of the package whereby individual sutures may be grasped and withdrawn from the package without entangling sutures remaining in the package. Each suture may be multifilament or monofilament, and may have a needle attached to the end extending from the package.

The suture package may be formed of paper or plastic or other suitable material and is comprised of at least two panels and means for securing the panels together with the coiled sutures positioned therebetween. Particularly preferred is a foldable suture package constructed of a heavy weight, relatively stiff paper or paperboard such as 5 point or 12 point sold bleached sulfate board. The panels of such packages may employ integral locking means such as tabs and slots to secure the panels together, or alternatively, adhesive or mechanical fastening means may be used.

DESCRIPTION OF DRAWINGS

FIG. 1 is a plan view of one preferred suture package for use in the present invention.

FIG. 2 is a view in perspective of the suture package of FIG. 1 positioned over two suture winding pins having a plurality of individual suture strands wound thereon in a figure-8 pattern.

FIG. 3 is a view in perspective of the suture and package of FIG. 2 after the package has been folded to retain the coiled sutures between two panels.

FIG. 4 is a view in perspective of the package of FIG. 3 after being removed from the winding pins.

FIG. 5 is a transparent plan view of a plurality of adjacent sutures wound in the form of a figure-8 and retained in a suture package.

FIG. 6 is a view in perspective of two suture winding pins having a plurality of suture strands wound thereon in a circular pattern.

FIG. 7 is a view in perspective of two suture winding pins having a plurality of suture strands wound thereon in a combination of figure-8 and circular windings.

DESCRIPTION OF PREFERRED EMBODIMENTS

Suture packages of the present invention are characterized by a plurality of suture strands individually coiled in the form of a series of overlapping figure-8 or elongated circular, i.e., oval convolutions having a longitudinal axis and wound in sequence over the length of the suture, the longitudinal axis of each convolution lying in a plane and being laterally displaced so that adjacent convolutions are not superimposed directly one upon the other, and with individual sutures being laterally displaced from adjacent sutures in a contiguous and partially overlapping relationship within a single package compartment.

The desired suture configuration may be obtained by any convenient method. In a particularly preferred method, individual sutures are wound around two vertical pins beginning at the bottom of the pins and winding in an upwardly spiraling pattern so that every loop on the pin is above the next preceding loop. In this manner, overlapping of successive loops of individual sutures and of adjacent sutures is avoided and, when the pins are removed after means have been provided to maintain the sutures in their relative positions, the loops of individual sutures and of adjacent sutures are sequentially disposed and laterally displaced or offset one from the other.

The suture package may be of any construction effective to maintain the sutures in their desired coiled configuration and relative positions. Foldable suture packages are most conveniently used since the package may be open during the suture winding operation and then folded about the suture to retain the coiled suture before the supporting winding pins are removed.

Representative figure-8 and oval suture configurations and packages of the present invention will be more fully understood by reference to the several drawings which illustrate preferred package designs and method of winding multistrand sutures to obtain the desired suture coils which allows single strand delivery from a multistrand package in accordance with the present invention.

Turning now to FIG. 1, there is illustrated an open suture package blank adapted for packaging the coiled sutures of the present invention. The package is comprised of a foldable paperboard having five main panels identified as suture retaining panels 10 and 11, end panels 13 and 14, and cover panel 12. Panel 10 is foldably attached to panel 11 through gussets 15 which each contain a single circular opening 16. In addition, locking slot 20 is provided on the fold line between panels 10 and 11, locking tab 17 is provided on the outer edge of panel 10.

End panels 13 and 14 are foldably connected to panel 11 through hinge sections 24. Each panel includes a locking tab 22, and 14 additionally contains cutout 21 to provide an opening for removing sutures from the package.

Cover panel 12 is foldably connected to panel 11 through gussets 15. As illustrated, panel 12 contains three package locking slots identified as 18, 19 and 23, the function of which is hereinafter described.

FIG. 2 illustrates the package of FIG. 1 with suture winding pins 26 projecting upward through holes 16 and with a plurality of sutures 25 sequentially wound upon pins 16 in an upwardly spiraling figure-8 configuration. In winding the individual sutures around pins 26, care is taken to avoid overlapping adjacent suture loops.

FIG. 3 illustrates the suture package of FIG. 2 with the coiled suture retained between panel 11 and end panels 13 and 14 which have been folded inwardly over the suture coil. Tabs 22 of end panels 13 and 14 are locked in slot 23 of panel 12. The ends of the individual sutures 25 project from the package through cutout 21 and panel 14.

FIG. 4 illustrates the package of FIG. 3 with panel 10 additionally folded over end panels 13 and 14 and locked in position by means of tab 17 being inserted through locking slot 18. The sutures extend from the package through cutout 29 in the end section of panel 10. FIG. 4 additionally illustrates needles 27 attached to the end of the sutures 25 extending from the package. To complete the package, needles 27 and attached suture ends are folded back onto the outer surface of panel 10 and covered by panel 12 which folds forward over panel 10 and locks by inserting tab 19 into slot 20, whereby the needled ends of the suture are maintained within the confines of the package.

The configuration of the individually coiled sutures within the package is illustrated by FIG. 5 which shows five individual sutures coiled in accordance with the present invention and retained in a package comprising cover panel 32 heat sealed around peripheral border 30 to backing panel 33. Panel 33 is extended beyond panel 32 and adapted to be folded forward over panel 32 with tab 34 interlocking along edge 28 whereby the ends of sutures 25 are folded back over panel 32 and enclosed within the package. When panel 33 is opened, the ends of sutures 25 are readily available for grasping and individual sutures may be withdrawn from between panels 32 and 33 through opening 35. Openings 31 in heat seal border 30 are openings for the suture winding pins and may be sealed if desired once the pins are removed.

FIG. 6 illustrates winding pins 26 having a plurality of sutures 25 wound in the form of an upwardly spiraling circular coil. For the sake of clarity, the suture folder shown in FIG. 1 is omitted, and the spacing of individual sutures on the winding pins is exaggerated.

FIG. 7 illustrates a plurality of sutures 25 wound about pins 26 in a combination of circular and crossing coils. As in FIG. 6, the suture folder is omitted and adjacent sutures are spaced widely apart for clarity of illustration.

The fabrication of the suture package of FIG. 5 by heat sealing is well-known in the art as described, for example, in U.S. Pat. No. 3,221,873, which is incorporated herein by reference for its teaching of materials and procedures in this regard. With further reference to FIG. 5, panel 32 is preferably a transparent heat sealable film or laminate while panel 33 is preferably paperboard, having a heat sealable coating thereon. As will be apparent to those skilled in the art, many variations in package design, materials and construction are permissible in providing the packages of the present invention. For example, panels 32 and 33 may be joined by the use of an adhesive applied to the panels in the areas to be joined. The present invention is accordingly not limited by any particular package composition or structure.

Although the sutures are wound on the winding pins in a sequential, nonoverlapping configuration, it will be appreciated that when the winding pins are removed and the coiled sutures are contained between the two panels of the package, the sutures assume the configuration as illustrated in FIG. 5. In particular, overlapping convolutions within a single suture coil are laterally displaced from adjacent convolutions and disposed in sequence from one end of the suture to the other. At the same time, the coils of each individual suture assume a contiguous and partially overlapping relationship with the coils of adjacent sutures. The contiguous and partially overlapping relationship of adjacent sutures within a single package compartment distinguishes sutures packaged in accordance with the present invention from similar packages wherein individual sutures are packaged in adjacent but separate compartments and in a spaced-apart relationship as, for example, in U.S. Pat. No. 3,857,484.

Sutures packaged in groups of 3 to 8 strands or more may be individually removed from the packages of the present invention by simply grasping an exposed end of any single suture and withdrawing the suture with a steady pull. The unique positioning of the sutures within the package allows individual suture strands to be withdrawn from the package without entangling the remaining sutures.

Sutures packaged in accordance with the present invention may be multifilament or monofilament sutures and multifilament sutures may be braided, twisted or covered. In addition, these sutures may be packaged with or without needles attached to the end of the suture which extends from the package.

While the foregoing has described a package construction and method for winding and loading sutures into the package in accordance with a preferred embodiment of the present invention, many variations will be apparent to those skilled in the art. For example, the sutures may be wound on any apparatus which will provide the suture coil configurations illustrated in FIGS. 5–7. Once so wound, the suture may be loaded into any package which will effectively maintain the sutures in the desired configuration and provide access to one end of individual sutures to permit withdrawal of the sutures from the package.

I claim:

1. A multistrand suture package providing individual suture delivery comprising a plurality of suture strands, each strand being individually coiled in a series of overlapping elongated convolutions disposed in sequence from one end of the suture to the other, each convolution having a longitudinal axis lying in a plane, the longitudinal axis of adjacent convolutions of each suture strand being substantially parallel and laterally displaced from each other in said plane, and each individual suture being laterally displaced from adjacent sutures in a contiguous and partially overlapping relationship, and suture retaining means comprising a common suture compartment within said package, said suture strands being retained in said compartment in the aforesaid configuration with one end of each suture extending from said compartment, whereby individual suture strands may be grasped and withdrawn from said compartment without entangling sutures remaining in the compartment.

2. A package of claim 1 wherein said suture strands are coiled in a series of figure-8 convolutions.

3. A package of claim 1 wherein said suture strands are coiled in a series of oval convolutions.

4. A package of claim 1 wherein said suture strands are coiled in a series of circular convolutions having at least one reversal in the direction of winding.

5. A package of claim 1 wherein said suture strands have needles attached to the end extending from said compartment.

6. A package of claim 1 comprising a plurality of multifilament braided suture strands.

7. A package of claim 6 wherein said suture strands have needles attached.

8. A package of claim 1 wherein said retaining means comprises first and second panels foldably connected and adapted to hold the suture coils therebetween in a common suture compartment when said panels are in a folded position, and means associated with said panels for holding said panels in said folded position.

9. A suture package according to claim 8 wherein the means for holding said panels in a folded position comprise a locking tab along a free edge of one panel which enters into alignment with and engages a locking slot in the other panel when said panels are in a folded position.

10. A suture package according to claim 8 wherein the means for holding said panels in a folded position comprise stapling means.

11. A suture package according to claim 8 wherein the means for holding said panels in a folded position comprise adhesive means.

12. A package of claim 8 wherein the ends of the suture strands extending from the common suture compartment extend from between said first and second panels and are returned back over said second panel, and said package additionally comprises a third panel foldably attached to said first panel and adapted to be folded down over said suture ends to retain said ends in the aforesaid position over said second panel, and means associated with said third panel for holding said panel in said folded position.

13. A package of claim 12 wherein said suture strands have needles attached to the ends retained by said third panel.

14. A package of claim 1 wherein said retaining means comprise a first rectangular panel having major and minor edges, second and third panels foldably connected to said first panel along the minor edges thereof, and a fourth panel foldably connected to said first panel along one major edge thereof, said second and third panels being adapted to fold inwardly over said first panel to form a common suture compartment with said suture strands retained therein and said fourth panel being adapted to fold over said second and third panel, and means for holding said panels in the aforesaid folded positions.

15. A package of claim 14 wherein said second and third panels have locking tabs and said first panel has a locking slot, said tabs and slot entering into alignment and engaging one another when said second and third panels are folded over said first panel.

16. A package of claim 14 wherein said fourth panel has a locking tab and said first panel has a locking slot, said tab and slot entering into alignment and engaging one another when said fourth panel is folded over said second and third panels.

17. A package of claim 1 wherein said retaining means comprises first and second rectangular panels having the suture coils positioned therebetween, said panels being joined around the periphery of three sides to form a single suture compartment having an opening on one side thereof, said suture strands being enclosed within said compartment with one end extending from the compartment through the opening thereof.

18. A package of claim 17 wherein said first and second panels are joined by a heat seal.

19. A package of claim 17 wherein said first and second panels are joined by an adhesive.

* * * * *